(12) United States Patent
Song

(10) Patent No.: US 8,044,257 B2
(45) Date of Patent: Oct. 25, 2011

(54) ABSORBENT ARTICLE CONTAINING LATERAL FLOW ASSAY DEVICE

(75) Inventor: Xuedong Song, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1032 days.

(21) Appl. No.: 11/589,671

(22) Filed: Oct. 30, 2006

(65) Prior Publication Data
US 2008/0103414 A1    May 1, 2008

(51) Int. Cl.
*A61F 13/15* (2006.01)
*A61F 13/20* (2006.01)

(52) U.S. Cl. ....................................................... 604/361

(58) Field of Classification Search ................... 604/361
See application file for complete search history.

(56) References Cited

U.S. PATENT DOCUMENTS

| | | | |
|---|---|---|---|
| 3,802,842 A | 4/1974 | Lange et al. | |
| 4,637,979 A | 1/1987 | Skjold et al. | |
| 4,657,855 A | 4/1987 | Corey et al. | |
| 4,670,381 A | 6/1987 | Frickey et al. | |
| 4,704,116 A | 11/1987 | Enloe | |
| 4,738,674 A * | 4/1988 | Todd et al. | 604/361 |
| 4,806,423 A | 2/1989 | Hugl et al. | |
| 4,814,271 A | 3/1989 | Hugl et al. | |
| 5,075,077 A | 12/1991 | Durley, III et al. | |
| 5,192,606 A | 3/1993 | Proxmire et al. | |
| 5,252,459 A | 10/1993 | Tarcha et al. | |
| 5,399,219 A | 3/1995 | Roessler et al. | |
| 5,464,739 A | 11/1995 | Johnson et al. | |
| 5,468,236 A | 11/1995 | Everhart et al. | |
| 5,486,166 A | 1/1996 | Bishop et al. | |
| 5,490,846 A | 2/1996 | Ellis et al. | |
| 5,540,796 A | 7/1996 | Fries | |
| 5,595,618 A | 1/1997 | Fries et al. | |

(Continued)

FOREIGN PATENT DOCUMENTS

DE    4403437 A1    8/1995

(Continued)

OTHER PUBLICATIONS

Article —*Concurrent Engineering for Lateral-Flow Diagnostics*, Alan Weiss, IVD Technology Magazine, 6 pages, www.devicelink.com.

(Continued)

*Primary Examiner* — Melanie Hand
(74) *Attorney, Agent, or Firm* — Dority & Manning, P.A.

(57) ABSTRACT

An absorbent article that contains a lateral flow assay device for testing a bodily fluid, such as urine, blood, mucous, saliva, etc., is provided. The lateral flow assay device includes a chromatographic medium (e.g., porous membrane) that defines a detection zone that provides a signal indicative of the presence or absence of the analyte. The device may also include a control zone that provides a signal indicative of whether a sufficient amount of bodily fluid has been provided and tested. Regardless of its specific configuration, the lateral flow assay device is integrated into the absorbent article to provide a user or caregiver with rapid information about a health condition. For example, the device may be integrated into a diaper to provide information about the presence of enzymes or other compounds often encountered with a patient having a urinary tract infection. This information may provide an early warning system to allow the user or caregiver to seek additional testing and/or treatment. Alternatively, semi-quantitative or quantitative results may be derived from the test.

22 Claims, 4 Drawing Sheets

U.S. PATENT DOCUMENTS

| | | | |
|---|---|---|---|
| 5,663,044 | A | 9/1997 | Noffsinger et al. |
| 5,702,377 | A | 12/1997 | Collier, IV et al. |
| 5,750,359 | A | 5/1998 | Huh et al. |
| 5,989,921 | A | 11/1999 | Charlton et al. |
| 6,060,638 | A | 5/2000 | Paul et al. |
| 6,150,002 | A | 11/2000 | Varona |
| 6,203,496 | B1 | 3/2001 | Gael et al. |
| 6,464,635 | B1 | 10/2002 | Jimenez Cerrato et al. |
| 6,490,846 | B2 | 12/2002 | Koppe |
| 6,515,194 | B2 | 2/2003 | Neading et al. |
| 6,663,611 | B2 | 12/2003 | Blaney et al. |
| 6,713,660 | B1 | 3/2004 | Roe et al. |
| 7,094,528 | B2 | 8/2006 | Song et al. |
| 2003/0119073 | A1 | 6/2003 | Quirk et al. |
| 2003/0124739 | A1 | 7/2003 | Song et al. |
| 2003/0158530 | A1 | 8/2003 | Diehl et al. |
| 2004/0102750 | A1 | 5/2004 | Jameson |
| 2005/0054255 | A1 | 3/2005 | Morman et al. |
| 2005/0059941 | A1 | 3/2005 | Baldwin et al. |
| 2005/0124072 | A1 | 6/2005 | Boga et al. |
| 2006/0003336 | A1 | 1/2006 | Song et al. |
| 2006/0003394 | A1 | 1/2006 | Song |
| 2006/0025732 | A1 | 2/2006 | Ying et al. |
| 2007/0048807 | A1 | 3/2007 | Song |
| 2007/0048815 | A1 | 3/2007 | Song |
| 2007/0048816 | A1 | 3/2007 | Song |

FOREIGN PATENT DOCUMENTS

| | | |
|---|---|---|
| EP | 1034758 A1 | 9/2000 |
| GB | 2183160 A | 6/1987 |
| WO | WO 9516425 A1 | 6/1995 |
| WO | WO 0065348 A2 * | 11/2000 |
| WO | WO 0065348 A3 | 11/2000 |
| WO | WO 0113109 A2 | 2/2001 |
| WO | WO 2006118622 A1 | 11/2006 |

OTHER PUBLICATIONS

Search Report and Written Opinion for PCT/IB2007/053462.

Abstract of JP3210193 Measuring Instrument for Hydrolase, Sep. 13, 1991.

U.S. Appl. No. 11/302,991, filed Dec. 14, 2005, DiGiammarino, III et al., Detection of Secreted Lipase Proteins From *Candida* Species.

U.S. Appl. No. 11/012,759, filed Dec. 15, 2004, Kaylor et al., Sample-Efficient Lateral Flow Immunoassay.

U.S. Appl. No. 11/399,687, filed Apr. 6, 2006, Song, Enzymatic Detection Techniques.

U.S. Appl. No. 11/513,898, filed Aug. 30, 2006, Sayre et al., Detection of Hydrogen Peroxide Released by Enzyme-Catalyzed Oxidation of an Analyte.

U.S. Appl. No. 11/638,760, filed Dec. 14, 2006, Boga et al., Detection of Formaldehyde in Urine Samples.

U.S. Appl. No. 11/640,116, filed Dec. 15, 2006, Song, Lateral Flow Assay Device and Absorbent Article Containing Same.

U.S. Appl. No. 11/640,100, filed Dec. 15, 2006, Song et al., Indicator Immobilization on Assay Devices.

U.S. Appl. No. 11/640,458, filed Dec. 15, 2006, Song, Enzyme Detection Techniques.

* cited by examiner

ABSORBENT ARTICLE CONTAINING LATERAL FLOW ASSAY DEVICE

BACKGROUND OF THE INVENTION

Multiple tests have been developed for detecting components in urine. Such tests can provide information about overall health as well as provide an indication of a health problem. When timely administered, such tests may also be able to provide an early indication of a health problem, which may be very advantageous for effective treatment. By way of examples, urine testing can be used to detect urinary tract infections, diabetes (including diabetic ketoacidosis), parasites, dehydration, dietary defects, cancer, high blood pressure, kidney disease, asthma, severe emphysema, alcoholism, systemic lupus erythematosus (SLE), glomerulonephritis, and leukemia.

Such tests may be performed by having a patient voluntarily collect and provide a sample. However, patient collected urine samples may not be readily available with certain test subjects such as children, elderly adults, and injured or non-ambulatory patients. Additionally, it may be preferable to collect and test urine samples from these subjects at certain times or conditions where the patient is not necessarily in the presence of medical or otherwise specially trained personnel. Frequently, such subjects may be provided with a diaper or other absorbent article to collect urine and provide for disposal in a hygienic manner. Of course, these articles must be periodically checked to determine whether urine and other bodily waste has been collected.

Specific developments have been provided for collecting and detecting urine samples using a diaper and/or an absorbent article. By way of example, U.S. Pat. No. 6,713,660 indicates a disposable article that includes a biosensor adapted to detect a specific biological analyte in bodily waste. U.S. Pat. No. 6,203,496 indicates a disposable diaper having one or more chemical reagents applied to the absorbent region that change color when certain components are present. U.S. Pat. No. 5,468,236 indicates a disposable absorbent product that includes a chemically reactive means that is applied, for example, to one or more layers of the absorbent product.

Despite these developments for absorbent articles, a need for improvement remains. An absorbent article that includes a device not only capable of testing a bodily fluid such as urine for one or more particular component(s) but also equipped for indicating that such fluid has been collected and tested would be particularly beneficial. Additionally, an absorbent article that can also provide, in certain embodiments, an effective urine test for detecting and reporting a urinary tract infection would also be particularly beneficial.

SUMMARY OF THE INVENTION

In accordance with one embodiment of the present invention, an absorbent article for receiving a bodily fluid suspected of containing an analyte is disclosed. The article comprises a substantially liquid impermeable layer; a liquid permeable layer; an absorbent core positioned between the substantially liquid impermeable layer and the liquid permeable layer; and a lateral flow assay device integrated into the article and positioned such that the device is in fluid communication with the bodily fluid when provided by a wearer of the article. The lateral flow assay device comprises a chromatographic medium that defines a detection zone, the detection zone being configured for exhibiting a signal indicative of the presence or absence of the analyte in the bodily fluid.

In accordance with another embodiment of the present invention, a method of detecting the presence of an analyte within a bodily fluid is disclosed. The method comprises providing an absorbent article having a lateral flow assay device, the lateral flow assay device comprising a chromatographic medium that defines a detection zone, the detection zone being configured to provide a visual detection signal indicative of the presence or absence of the analyte within the bodily fluid. The absorbent article is contacted with the bodily fluid, and the detection zone is observed for the visual detection signal.

Other features and aspects of the present invention are described in more detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1:
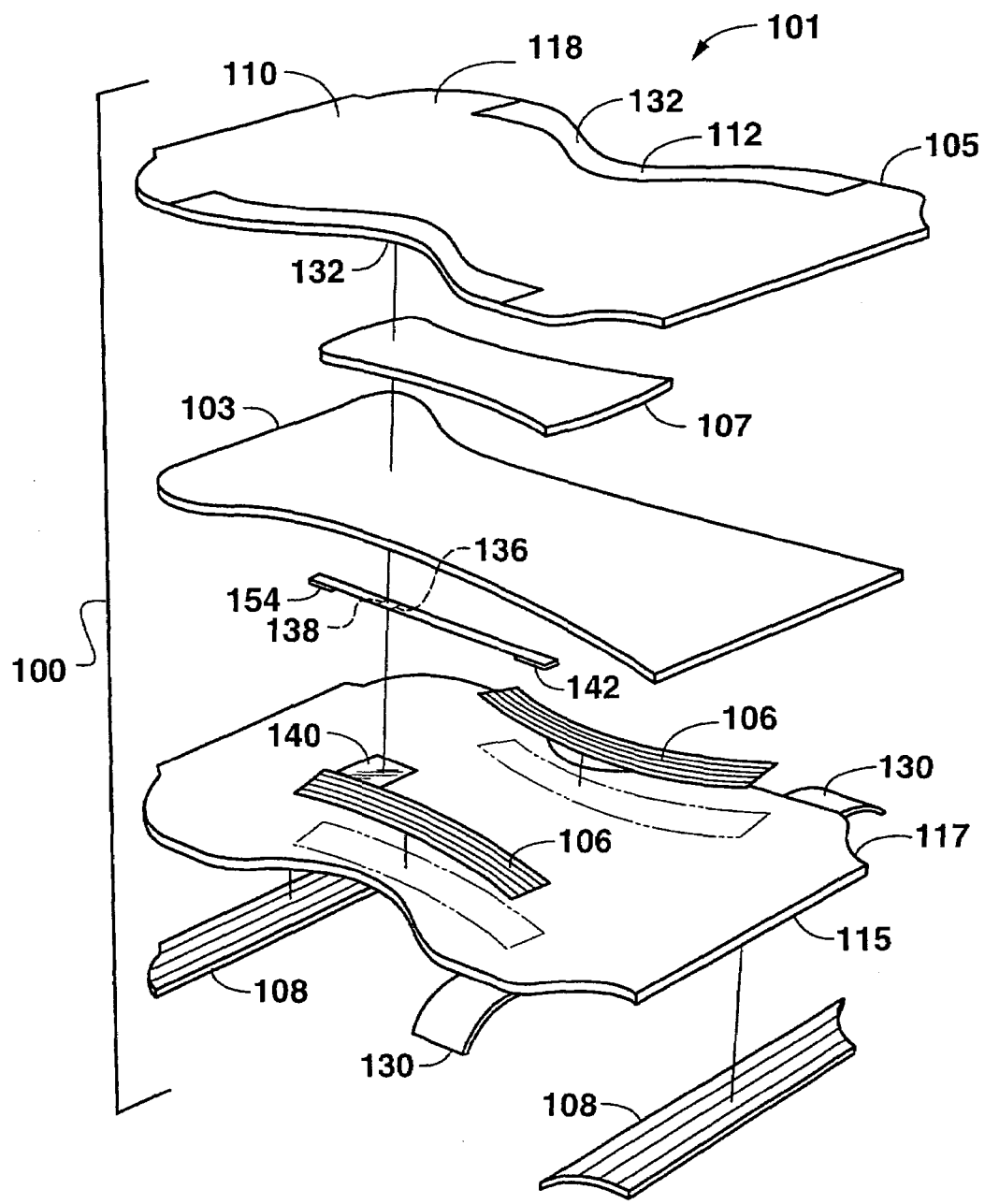
FIG. 1 is an exploded view of an exemplary embodiment according to the present invention.

Repeat use of reference characters in the present specification and drawings is intended to represent same or analogous features or elements of the invention.

DETAILED DESCRIPTION OF REPRESENTATIVE EMBODIMENTS

Reference now will be made in detail to various embodiments of the invention, one or more examples of which are set forth below. Each example is provided by way of explanation, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention cover such modifications and variations.

Generally speaking, the present invention is directed to an absorbent article that contains a lateral flow assay device for testing a bodily fluid, such as urine, blood, mucous, saliva, etc. The lateral flow assay device includes a chromatographic medium (e.g., porous membrane) that defines a detection zone that provides a signal indicative of the presence or absence of the analyte. The device may also include a control zone that provides a signal indicative of whether a sufficient amount of bodily fluid has been provided and tested. Regardless of its specific configuration, the lateral flow assay device is integrated into the absorbent article to provide a user or caregiver with rapid information about a health condition. For example, the device may be integrated into a diaper to provide information about the presence of enzymes or other compounds often encountered with a patient having a urinary tract infection. This information may provide an early warning system to allow the user or caregiver to seek additional testing and/or treatment. Alternatively, semi-quantitative or quantitative results may be derived from the test.

Various embodiments of the present invention will now be described in more detail.

I. Lateral Flow Assay Device

Generally speaking, a lateral flow assay device is employed in the present invention to perform a heterogeneous assay. A heterogeneous assay is one in which species is separated from another species prior to detection. Separation may be carried out by physical separation, e.g., by transferring one of the species to another reaction vessel, filtration, centrifugation, chromatography, solid phase capture, magnetic separation, and so forth. The separation may also be nonphysical in that no transfer of one or both of the species is conducted, but the species are separated from one another in situ. In some embodiments, for example, a heterogeneous immunoassay is performed that utilizes mechanisms of the immune systems, wherein antibodies are produced in response to the presence of antigens that are pathogenic or foreign to the organisms. These antibodies and antigens, i.e., immunoreactants, are capable of binding with one another, thereby causing a highly specific reaction mechanism that may be used to determine the presence or concentration of that particular antigen in a fluid test sample. In other embodiments, however, the heterogeneous assay may employ non-specific chemical reactions to achieve the desired separation.

Figure 6:
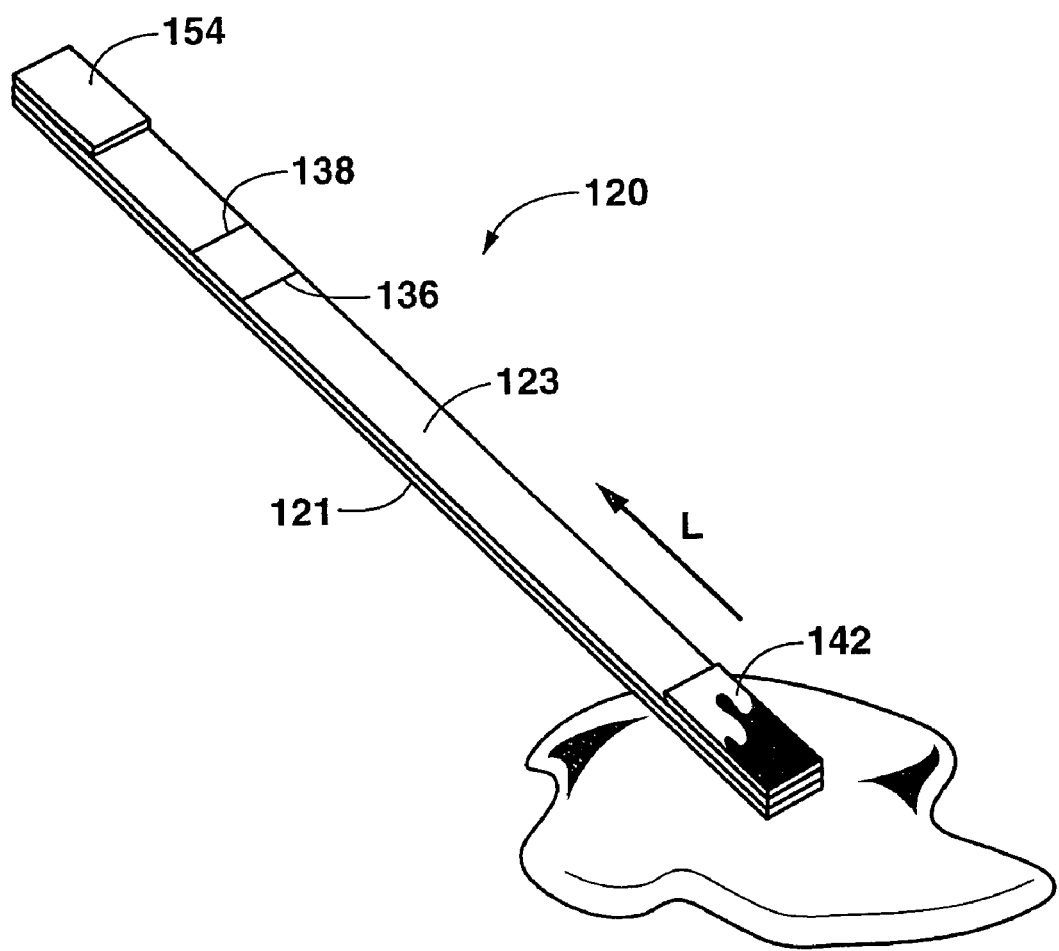
FIG. 6 is a perspective view that provides an example of a lateral flow assay device as may be used in certain exemplary embodiments of the present invention.

In any event, the use of a lateral flow assay device provides a variety of benefits, including a more uniform flow of the bodily fluid and reagents during testing. This may enhance the accuracy of the test and minimize the need for external control mechanisms. Referring to FIG. 6, for example, one embodiment of a lateral flow assay device 120 will now be described in more detail. As shown, the device 120 contains a chromatographic medium 123 optionally supported by a rigid support 121. The chromatographic medium 123 may be made from any of a variety of materials through which the test sample is capable of passing. For example, the chromatographic medium 123 may be a porous membrane formed from synthetic or naturally occurring materials, such as polysaccharides (e.g., cellulose materials such as paper and cellulose derivatives, such as cellulose acetate and nitrocellulose); polyether sulfone; polyethylene; nylon; polyvinylidene fluoride (PVDF); polyester; polypropylene; silica; inorganic materials, such as deactivated alumina, diatomaceous earth, $MgSO_4$, or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon or rayon); porous gels, such as silica gel, agarose, dextran, and gelatin; polymeric films, such as polyacrylamide; and so forth. In one particular embodiment, the chromatographic medium 123 is formed from nitrocellulose and/or polyether sulfone materials. It should be understood that the term "nitrocellulose" refers to nitric acid esters of cellulose, which may be nitrocellulose alone, or a mixed ester of nitric acid and other acids, such as aliphatic carboxylic acids having from 1 to 7 carbon atoms.

The size and shape of the chromatographic medium 123 may generally vary as is readily recognized by those skilled in the art. For instance, a porous membrane strip may have a length of from about 10 to about 100 millimeters, in some embodiments from about 20 to about 80 millimeters, and in some embodiments, from about 40 to about 60 millimeters. The width of the membrane strip may also range from about 0.5 to about 20 millimeters, in some embodiments from about 1 to about 15 millimeters, and in some embodiments, from about 2 to about 10 millimeters. Likewise, the thickness of the membrane strip is generally small enough to allow transmission-based detection. For example, the membrane strip may have a thickness less than about 500 micrometers, in some embodiments less than about 250 micrometers, and in some embodiments, less than about 150 micrometers.

As stated above, the support 121 carries the chromatographic medium 123. For example, the support 121 may be positioned directly adjacent to the chromatographic medium 123 as shown in FIG. 1, or one or more intervening layers may be positioned between the chromatographic medium 123 and the support 121. Regardless, the support 121 may generally be formed from any material able to carry the chromatographic medium 123. The support 121 may be formed from a material that is transmissive to light, such as transparent or optically diffuse (e.g., transluscent) materials. Also, it is generally desired that the support 121 is liquid-impermeable so that fluid flowing through the medium 123 does not leak through the support 121. Examples of suitable materials for the support include, but are not limited to, glass; polymeric materials, such as polystyrene, polypropylene, polyester (e.g., Mylar® film), polybutadiene, polyvinylchloride, polyamide, polycarbonate, epoxides, methacrylates, and polymelamine; and so forth. To provide a sufficient structural backing for the chromatographic medium 123, the support 121 is generally selected to have a certain minimum thickness. Likewise, the thickness of the support 121 is typically not so large as to adversely affect its optical properties. Thus, for example, the support 121 may have a thickness that ranges from about 100 to about 5,000 micrometers, in some embodiments from about 150 to about 2,000 micrometers, and in some embodiments, from about 250 to about 1,000 micrometers. For instance, one suitable membrane strip having a thickness of about 125 micrometers may be obtained from Millipore Corp. of Bedford, Mass. under the name "SHF180UB25."

The chromatographic medium 123 may be cast onto the support 121, wherein the resulting laminate may be die-cut to the desired size and shape. Alternatively, the chromatographic medium 123 may simply be laminated to the support 121 with, for example, an adhesive. In some embodiments, a nitrocellulose or nylon porous membrane is adhered to a Mylar® film. An adhesive is used to bind the porous membrane to the Mylar® film, such as a pressure-sensitive adhesive. Laminate structures of this type are believed to be commercially available from Millipore Corp. of Bedford, Mass. Still other examples of suitable laminate device structures are described in U.S. Pat. No. 5,075,077 to Durley, III, et al., which is incorporated herein in its entirety by reference thereto for all purposes.

The device 120 may also contain an absorbent material 154 that is positioned adjacent to the medium 123. The absorbent material 154 assists in promoting capillary action and fluid flow through the medium 123. In addition, the absorbent material 154 receives fluid that has migrated through the entire chromatographic medium 123 and thus draws any unreacted components away from the detection region to help reduce the likelihood of "false positives." Some suitable absorbent materials that may be used in the present invention include, but are not limited to, nitrocellulose, cellulosic materials, porous polyethylene pads, glass fiber filter paper, and so forth. The absorbent material may be wet or dry prior to being incorporated into the device. Pre-wetting may facilitate capillary flow for some fluids, but is not typically required. Also, as is well known in the art, the absorbent material may be treated with a surfactant to assist the wicking process.

To initiate the detection of an analyte, the bodily fluid (e.g., urine) may be applied to a portion of the chromatographic medium 123 through which it may then travel in the direction illustrated by arrow "L" in FIG. 6. Alternatively, the fluid may first contact a sample application zone 142 that is in fluid communication with the chromatographic medium 123. The sample application zone 142 may be defined by a separate pad or material as shown in FIG. 6, or simply defined by the chromatographic medium 123. In the illustrated embodiment, the fluid may travel from the sample application zone 142 to a conjugate pad (not shown) that is placed in communication with one end of the sample pad. The conjugate pad may contain one or more diffusively immobilized reagents, and be formed from a material through which a fluid is capable of passing (e.g., glass fibers). Some suitable materials that may be used to form the absorbent material 154 and/or sample pad include, but are not limited to, nitrocellulose, cellulose, porous polyethylene pads, and glass fiber filter paper. If desired, the sample pad may also contain one or more assay pretreatment reagents, either diffusively or non-diffusively attached thereto.

Regardless of the particular manner in which it is formed, the lateral flow assay device of the present invention employs one or more zones for providing an indicator of the presence of an analyte. More specifically, such zone(s) typically contain a chemical or biological reagent that interacts with the analyte and/or other reagents to generate a signal (e.g., visual signal). Referring again to FIG. 6, for example, the lateral flow assay device 120 includes a detection zone 136 within which a capture reagent is disposed. Typically, the capture reagent is applied in a manner so that it does not substantially diffuse through the matrix of the chromatographic medium 123 (i.e., non-diffusively immobilized). This enables a user to readily detect the change in color that occurs upon reaction of the capture reagent with other compounds. The capture reagent may, for example, form an ionic and/or covalent bond with functional groups present on the surface of the chromatographic medium 123 so that it remains immobilized thereon. For instance, particles, such as described below, may facilitate the immobilization of the reagent at the detection zone 136. Namely, the reagent may be coated onto particles, which are then immobilized on the chromatographic medium 123 of the device 120. In this manner, the reagent is able to readily contact compounds flowing through the medium 123.

Another zone that may be employed in the lateral flow assay device 120 for improving detection accuracy is a control zone 138. The control zone 138 gives a signal to the user that the test is performing properly. More specifically, reagents may be employed that flow through the chromatographic medium 123 upon contact with a sufficient volume of the bodily fluid being tested. These reagents may then be observed, either visually or with an instrument, within the control zone 138. The control reagents generally contain a detectable substance, such as luminescent compounds (e.g., fluorescent, phosphorescent, etc.); radioactive compounds; visual compounds (e.g., colored dye or metallic substance, such as gold); liposomes or other vesicles containing signal-producing substances; enzymes and/or substrates, and so forth. Other suitable detectable substances may be described in U.S. Pat. No. 5,670,381 to Jou, et al. and U.S. Pat. No. 5,252,459 to Tarcha, et al., which are incorporated herein in their entirety by reference thereto for all purposes.

If desired, one or more of the reagents employed in the assay device may be disposed on particles (sometimes referred to as "beads" or "microbeads"). Among other things, the particles enhance the ability of the reagent to travel through a chromatographic medium. For instance, naturally occurring particles, such as nuclei, mycoplasma, plasmids, plastids, mammalian cells (e.g., erythrocyte ghosts), unicellular microorganisms (e.g., bacteria), polysaccharides (e.g., agarose), etc., may be used. Further, synthetic particles may also be utilized. For example, in one embodiment, latex microparticles that are labeled with a fluorescent or colored dye are utilized. Although any synthetic particle may be used in the present invention, the particles are typically formed from polystyrene, butadiene styrenes, styreneacrylic-vinyl terpolymer, polymethylmethacrylate, polyethylmethacrylate, styrene-maleic anhydride copolymer, polyvinyl acetate, polyvinylpyridine, polydivinylbenzene, polybutyleneterephthalate, acrylonitrile, vinylchloride-acrylates, and so forth, or an aldehyde, carboxyl, amino, hydroxyl, or hydrazide derivative thereof. When utilized, the shape of the particles may generally vary. In one particular embodiment, for instance, the particles are spherical in shape. However, it should be understood that other shapes are also contemplated by the present invention, such as plates, rods, discs, bars, tubes, irregular shapes, etc. In addition, the size of the particles may also vary. For instance, the average size (e.g., diameter) of the particles may range from about 0.1 nanometers to about 1,000 microns, in some embodiments, from about 0.1 nanometers to about 100 microns, and in some embodiments, from about 1 nanometer to about 10 microns. Commercially available examples of suitable particles include fluorescent carboxylated microspheres sold by Molecular Probes, Inc. under the trade names "FluoSphere" (Red 580/605) and "Transfluo-Sphere" (543/620), as well as "Texas Red" and 5- and 6-carboxytetramethylrhodamine, which are also sold by Molecular Probes, Inc. In addition, commercially available examples of suitable colored, latex microparticles include carboxylated latex beads sold by Bang's Laboratory, Inc.

The location of the detection zone 136 and control zone 138 may vary based on the nature of the test being performed. In the illustrated embodiment, for example, the control zone 138 is defined by the chromatographic medium 123 and positioned downstream from the detection zone 136. In such embodiments, the control zone 138 may contain a material that is non-diffusively immobilized in the manner described above and forms a chemical and/or physical bond with the control reagents. When the control reagents contain latex particles, for instance, the control zone 138 may include a polyelectrolyte that binds to the particles. Various polyelectrolytic binding systems are described, for instance, in U.S. Patent App. Publication No. 2003/0124739 to Song, et al., which is incorporated herein in it entirety by reference thereto for all purposes. In alternative embodiments, however, the control zone 138 may simply be defined by a region of the absorbent material 154 to which the control reagents flow after traversing through the chromatographic medium 123.

Regardless of the particular control technique selected, the application of a sufficient volume of the test sample to the device 120 will cause a signal to form within the control zone 138, whether or not the enzyme or other analyte of interest is present. Among the benefits provided by such a control zone is that the user or other personnel are informed that a sufficient volume of test sample has been added without requiring careful measurement or calculation. This provides the ability to use the lateral flow assay device 120 without the need for externally controlling the reaction time, test sample volume, etc. In the case of the elderly, children, or patients unable to communicate clearly, control zone 138 provides an indication that a sample was discharged, collected, and successfully tested.

The detection zone 136, control zone 138, or any other zone employed in the lateral flow assay device 120 may generally provide any number of distinct detection regions so that a user may better determine the concentration of the enzyme or other analyte within the test sample. Each region may contain the same or different materials. For example, the zones may include two or more distinct regions (e.g., lines, dots, etc.). The regions may be disposed in the form of lines in a direction that is substantially perpendicular to the flow of the test sample through the device 120. Likewise, in some embodiments, the regions may be disposed in the form of lines in a direction that is substantially parallel to the flow of the test sample through the device 120.

The specific reagents employed in the lateral flow assay device depend on the analyte of interest and the assay technique employed. In one particular embodiment, for example, it may be desirable to detect the presence of leukocytes in urine as an early diagnosis of urinary tract infection ("UTI"). Although leukocytes are normally present in the urine, it has been determined that the threshold limit for pathological levels is about $1\times10^4$ leukocytes per milliliter of uncentrifuged urine. When leukocytes are present in urine, leukocyte esterase is produced and may be used as a biomarker for the presence of leukocytes.

A variety of reagents may be used for detecting the presence of the leukocyte esterase enzyme. One such reagent is a substrate that is chemically acted upon or "cleaved" by the enzyme of interest to release a product. For example, the substrate may be an ester that is catalytically hydrolyzed in the presence of leukocyte esterase to yield an aromatic compound. The aromatic esters may include, for instance, indoxyl esters having the following general formula:

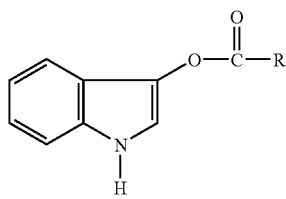

wherein, R may be substituted or unsubstituted, and may be an alkyl group, an alkyoxy group, a hydroxyalkyl group, an alkylene group, a fatty acid group, and so forth. In addition, the aromatic rings may also be substituted or unsubstituted. Specific examples include, for instance, indoxyl acetate, indoxyl butyrate, indoxyl laureate, indoxyl stearate, indoxyl ester of a N-blocked amino acid or peptide and thioindoxyl analogs thereof, and N-Tosyl-L-alanine 3-indoxyl ester. Such indoxyl esters are hydrolyzed by the leukocyte esterase to form a benzopyrrole, such as indoxyl, which has the following structure:

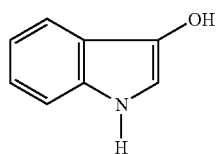

Lactate esters may also be used, such as described in U.S. Pat. No. 5,464,739 to Johnson, et al. and U.S. Pat. No. 5,663,044 to Noffsinger, et al., which are incorporated herein in their entirety by reference thereto for all purposes. Lactate esters are generally hydrolyzed by the leukocyte esterase to provide a hydroxy-pyrrole compound. Other suitable ester substrates include thiazole esters, pyrrole esters, thiophene esters, naphthyl esters, phenoxyl esters, quinolinyl esters, such as described in U.S. Pat. No. 5,750,359 to Huh, et al.; U.S. Pat. No. 4,657,855 to Corey, et al.; and Japanese Publication No. 03210193 to Kawanishi, et al., which are incorporated herein in their entirety by reference thereto for all purposes.

Typically, the substrate is diffusively immobilized on the lateral flow assay device 120 prior to application of the urine or other bodily fluid. The substrate is preferably disposed downstream from the sample application zone 142. In this manner, the test sample is capable of mixing with the enzyme upon application. If desired, the pH may be maintained at a relatively neutral level to facilitate the desired enzyme-catalyzed reaction, such as described above. To accomplish the desired pH level, a buffer may be mixed with the substrate prior to application to the device 120. Alternatively, the buffer may be separately applied to the lateral flow assay device 120 so that it is capable of mixing with the reagents upon exposure the bodily fluid being tested.

Regardless, an aromatic compound is released through cleavage of the substrate that is capable of inducing a color change in the presence of certain reagents. The released aromatic compound is a nucleophile in that it contains a group that is electron rich (e.g., amine) and that may form bonds with electron deficient groups. For example, indoxyl esters are hydrolyzed by the leukocyte esterase to form indoxyl. Indoxyl contains an electron-rich, aromatic ring system that is capable of undergoing electrophilic attack by a diazonium ion having the generic formula:

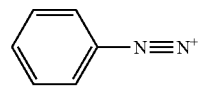

The diazonium ion may be zwitterionic in that the counterion of the diazonium moiety is covalently bound to the ring system. The ring system of the diazonium ion may be substituted or unsubstituted. The ion may be provided by a variety of suitable diazonium salts, such as diazonium chlorides, diazonium acid sulphates, diazonium alkyl sulphates, diazonium fluoborates, diazonium benzenesulphonates, diazonium acid 1,5-naphthalenedisulphonates, and so forth. Specific examples of diazonium salts are 1-diazo-2-naphthol-4-sulfonate; 1-diazophenyl-3-carbonate; 4-diazo-3-hydroxy-1-naphthylsulfonate (DNSA); 4-diazo-3-hydroxy-7-nitro-1-naphthylsulfonate (NDNSA); 4-diazo-3-hydroxy-1,7-naphthyldisulfonate; 2-methoxy-4-(N-morpholinyl) benzene diazonium chloride; 4-diazo-3-hydroxy-7-bromo-1-naphthylsulfonate; and 4-diazo-3-hydroxy-7-[1,oxopropyl]-1-naphthylsulfonate. One particularly desired diazonium salt is 5-chloro-2-methoxybenzenediazonium chloride, which has a yellow color and is classified under the name "Diazo Red RC" or "Fast Red RC." More specifically, "Fast Red RC" has the following structure:

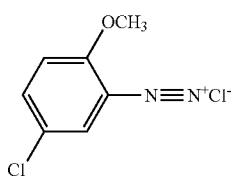

Other suitable diazonium salts are classified by the common names "Fast Red B" and "Fast Blue B." Still other suitable diazonium salts may be described in U.S. Pat. No. 4,637,979 to Skjold, et al.; U.S. Pat. No. 4,806,423 to Hugh, et al.; and U.S. Pat. No. 4,814,271 to Hugl, et al., which are incorporated herein in their entirety by reference thereto for all purposes.

As indicated above, the nucleophilic aromatic compounds released by the hydrolysis of the substrate are capable of undergoing electrophilic attack by a reagent (e.g., diazonium ion). This reaction is often referred to as "coupling" and results in the formation of another reagent having a different color. For example, diazonium ions may react with aromatic compounds to form an aromatic azo compound having the generic formula, R—N=N—R', wherein "R" and "R'" are aryl groups. Without intending to be limited by theory, it is believed that this reaction induces either a shift of the absorption maxima towards the red end of the spectrum ("bathochromic shift") or towards the blue end of the spectrum ("hypsochromic shift"). The type of absorption shift depends on the nature of the resulting azo molecule and whether it functions as an electron acceptor (oxidizing agent), in which a hypsochromic shift results, or whether it functions as an electron donor (reducing agent), in which a bathochromic shift results. The absorption shift provides a color difference that is detectable, either visually or through instrumentation, to indicate the presence of leukocyte esterase or other enzymes within the test sample. For example, prior to contact with an infected test sample, the diazonium ion may be colorless or it may possess a certain color. However, after contacting the test sample and reacting with an aromatic compound released by hydrolysis of the substrate, an aromatic azo compound will form that exhibits a color that is different than the initial color of the diazonium ion. Exemplary aromatic azo compounds that may be formed include dimethyldiazene, diphenydiazene, 1-naphthyl-2-naphthyl diazene, 3-chlorophenyl-4-chlorophenyl diazene, methylvinyl diazene, and 2-naphthylphenyl diazene. In one particular embodiment, for instance, "Fast Red RC" (yellow), a diazonium ion, may react with indoxyl to form an aromatic azo compound that is red and has the following general structure (may be substituted or unsubstituted):

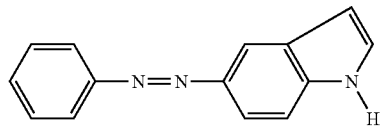

Normally, the above-described diazonium ion is immobilized within the detection zone 136 of the lateral flow assay device 120. The diazonium ion may be applied directly to the medium 123 or first formed into a solution prior to application. Various solvents may be utilized to form the solution, such as, but not limited to, acetonitrile, dimethylsulfoxide (DMSO), ethyl alcohol, dimethylformamide (DMF), and other polar organic solvents. For instance, the amount of a diazonium salt in the solution may range from about 0.001 to about 100 milligrams per milliliter of solvent, and in some embodiments, from about 0.1 to about 10 milligrams per milliliter of solvent. In one particular embodiment, the detection zone 136 is defined by the chromatographic medium 123 and formed by coating a solution thereon using well-known techniques and then dried. The diazonium ion concentration may be selectively controlled to provide the desired level of detection sensitivity.

Typically, the diazonium ion be applied in a manner so that it does not substantially diffuse through the matrix of the chromatographic medium 123 (i.e., non-diffusively immobilized). This enables a user to readily detect the change in color that occurs upon reaction of the diazonium ion with a nucleophilic aromatic compound. The diazonium ion may form an ionic and/or covalent bond with functional groups present on the surface of the chromatographic medium 123 so that it remains immobilized thereon. For instance, particles, such as described below, may facilitate the immobilization of the diazonium ion at the detection zone 136. Namely, the diazonium ion may be coated onto particles, which are then immobilized on the chromatographic medium 123 of the device 120. In this manner, the diazonium ion is able to readily contact nucleophilic aromatic compounds flowing through the medium 123.

One benefit of the lateral flow assay device is its ability to readily incorporate one or more additional reagent zones to facilitate the desired reactions. By way of example, a reagent zone (not shown) may be utilized. In the illustrated embodiment, the reagent zone may be located such that test sample travels from the sample application zone 142 to a reagent zone that is in fluid communication with the sample application zone 142. The reagent zone may be formed on the medium 123. Alternatively, the reagent zone may formed from a separate material or pad. Such a reagent pad may be formed from any material through which the test sample is capable of passing, such as glass fibers.

In addition to the zones specified above, the lateral flow assay device 120 may also include other optional zones. For example, the lateral flow assay device 120 may include an accelerator zone (not shown) in which is contained an accelerator for the enzyme-catalyzed substrate reaction. Typically, the accelerator is diffusively immobilized within the accelerator zone in the manner described above so that it may flow through the medium 123 upon contact with the test sample. The location of the accelerator zone may generally vary, so long as it positioned upstream from the detection zone 136. For example, in some embodiments, the accelerator zone may be positioned at a location (e.g., sample application zone 142) that is upstream from the application of the substrate (e.g., reagent zone). Due to the separation provided between the substrate and accelerator, the likelihood of any premature reaction therebetween is thus reduced. It should be understood, however, that the accelerator may nevertheless be combined with the substrate in some applications.

Another zone that may be employed is a quenching zone (not shown). The quenching zone is configured to remove compounds from the test sample that would otherwise interfere with the accuracy of the detection system. For example, contaminants within the test sample (e.g., phenolics, bilirubin, urobilinogen, etc.) may react with the diazonium ion within the detection zone 136 and form an aromatic azo compound, thereby producing a "false negative" result. Thus, the quenching zone may contain a quenching agent, such as a diazonium ion, that is capable of reacting with the reaction contaminants. The quenching agent may be the same or different than the detection agent used within the detection zone 136. Typically, the quenching agent is non-diffusively immobilized within the quenching zone in the manner described above so that it does not flow through the medium 123 and interfere with testing. The location of the quenching zone may vary, but is typically positioned upstream from the detection zone 136 and the location at which the substrate is applied to avoid interference with enzyme detection. For example, in the illustrated embodiment, the quenching zone may be positioned immediately downstream of the sample application zone 142 and over medium 123. Alternatively, the quenching zone 35 may be positioned upstream from the sample application zone 142.

An exemplary method for detecting the presence of leukocyte esterase within a test sample using the device 120 of FIG. 6 will now be described in more detail. Initially, urine containing leukocyte esterase is discharged to the sample application zone 142 and travels in the direction "L" to a reagent zone. At the reagent zone, the esterase is able to mix with and begin to initiate the catalytic reaction. While flowing through the medium, the enzyme and substrate react to release an aromatic product that subsequently couples with a diazonium ion to form a colored aromatic azo compound in the detection zone 136. After the reaction, the detection zone 136 changes color, which may be indicative of urinary tract infection. Due to the nature of the controlled fluid flow, any unreacted substrate travels to the end of the reaction medium so that it is unable to adversely interfere with observance of the aromatic azo compound in the detection region.

Of course, the present invention is by no means limited to the diagnosis of urinary tract infection. Numerous health conditions may be diagnosed through testing of bodily fluids such as urine. Testing for even a single condition may require that multiple different analytes be targeted. By way of example, the assay device may employ specific binding pairs to test for the presence of certain biological analytes (e.g., antibodies, antigens, etc.). Specific binding members generally refer to a member of a specific binding pair, i.e., two different molecules where one of the molecules chemically and/or physically binds to the second molecule. For instance, immunoreactive specific binding members may include antigens, haptens, aptamers, antibodies (primary or secondary), and complexes thereof, including those formed by recombinant DNA methods or peptide synthesis. An antibody may be a monoclonal or polyclonal antibody, a recombinant protein or a mixture(s) or fragment(s) thereof, as well as a mixture of an antibody and other specific binding members. The details of the preparation of such antibodies and their suitability for use as specific binding members are well known to those skilled in the art. Other common specific binding pairs include but are not limited to, biotin and avidin (or derivatives thereof), biotin and streptavidin, carbohydrates and lectins, complementary nucleotide sequences (including probe and capture nucleic acid sequences used in DNA hybridization assays to detect a target nucleic acid sequence), complementary peptide sequences including those formed by recombinant methods, effector and receptor molecules, hormone and hormone binding protein, enzyme cofactors and enzymes, enzyme inhibitors and enzymes, and so forth. Furthermore, specific binding pairs may include members that are analogs of the original specific binding member. For example, a derivative or fragment of the analyte, i.e., an analyte-analog, may be used so long as it has at least one epitope in common with the analyte.

Still other analytes of interest may include proteins, enzymes, nitrites, ketones, various bacteria, red or white blood cells, glucose, bilirubin, urobilinogen, and so forth. By way of example, the presence of nitrites in urine may indicate a urinary tract infection or even other bacterial infections in the body. To test for the presence of nitrites, the assay device may, for example, employ a substrate diffusively immobilized on the chromatographic medium that includes both an aromatic amine and another aromatic compound. The amine is selected so that it will react with the nitrite to form a diazonium salt. The salt, in turn, may react with the aromatic compound to generate an azo dye that provides a visual indication, by a color change, that nitrite has been detected.

II. Absorbent Article

In accordance with the present invention, one or more lateral flow assay devices are integrated into an absorbent article. An "absorbent article" generally refers to any article capable of absorbing water or other fluids. Examples of some absorbent articles include, but are not limited to, personal care absorbent articles, such as diapers, training pants, absorbent underpants, incontinence articles, feminine hygiene products (e.g., sanitary napkins), swim wear, baby wipes, and so forth; medical absorbent articles, such as garments, fenestration materials, underpads, bedpads, bandages, absorbent drapes, and medical wipes; food service wipers; clothing articles; and so forth. Materials and processes suitable for forming such absorbent articles are well known to those skilled in the art. Typically, absorbent articles include a substantially liquid-impermeable layer (e.g., outer cover), a liquid-permeable layer (e.g., bodyside liner, surge layer, etc.), and an absorbent core.

Various embodiments of an absorbent article that may be formed according to the present invention will now be described in more detail. For purposes of illustration only, an absorbent article is shown in FIG. 1 as a diaper 101. In the illustrated embodiment, the diaper 101 is shown as having an hourglass shape in an unfastened configuration. However, other shapes may of course be utilized, such as a generally rectangular shape, T-shape, or I-shape. As shown, the diaper 101 includes a chassis formed by various components, including an outer cover 117, bodyside liner 105, absorbent core 103, and surge layer 107. It should be understood, however, that other layers may also be used in exemplary embodiments of the present invention. Likewise, one or more of the layers referred to in FIG. 1 may also be eliminated in certain exemplary embodiments of the present invention.

The bodyside liner 105 is generally employed to help isolate the wearer's skin from liquids held in the absorbent core 103. For example, the liner 105 presents a bodyfacing surface that is typically compliant, soft feeling, and non-irritating to the wearer's skin. Typically, the liner 105 is also less hydrophilic than the absorbent core 103 so that its surface remains relatively dry to the wearer. As indicated above, the liner 105 may be liquid-permeable to permit liquid to readily penetrate through its thickness. Exemplary liner constructions that contain a nonwoven web are described in U.S. Pat. No. 5,192,606 to Proxmire, et al.; U.S. Pat. No. 5,702,377 to Collier, IV, et al.; U.S. Pat. No. 5,931,823 to Stokes, et al.; U.S. Pat. No. 6,060,638 to Paul, et al.; and U.S. Pat. No. 6,150,002 to Varona, as well as U.S. Patent Application Publication Nos. 2004/0102750 to Jameson; 2005/0054255 to Morman, et al.; and 2005/0059941 to Baldwin, et al., all of which are incorporated herein in their entirety by reference thereto for all purposes.

The diaper 101 may also include a surge layer 107 that helps to decelerate and diffuse surges or gushes of liquid that may be rapidly introduced into the absorbent core 103. Desirably, the surge layer 107 rapidly accepts and temporarily holds the liquid prior to releasing it into the storage or retention portions of the absorbent core 103. In the illustrated embodiment, for example, the surge layer 107 is interposed between an inwardly facing surface 116 of the bodyside liner 105 and the absorbent core 103. Alternatively, the surge layer 107 may be located on an outwardly facing surface 118 of the bodyside liner 105. The surge layer 107 is typically constructed from highly liquid-permeable materials. Examples of suitable surge layers are described in U.S. Pat. No. 5,486,166 to Ellis, et al. and U.S. Pat. No. 5,490,846 to Ellis, et al., which are incorporated herein in their entirety by reference thereto for all purposes.

The outer cover 117 is typically formed from a material that is substantially impermeable to liquids. For example, the outer cover 117 may be formed from a thin plastic film or other flexible liquid-impermeable material. In one embodiment, the outer cover 117 is formed from a polyethylene film having a thickness of from about 0.01 millimeter to about 0.05 millimeter. The film may be impermeable to liquids, but permeable to gases and water vapor (i.e., "breathable"). This permits vapors to escape from the absorbent core 103, but still prevents liquid exudates from passing through the outer cover 117. If a more cloth-like feeling is desired, the outer cover 117 may be formed from a polyolefin film laminated to a nonwoven web. For example, a stretch-thinned polypropylene film may be thermally laminated to a spunbond web of polypropylene fibers.

Besides the above-mentioned components, the diaper 101 may also contain various other components as is known in the art. For example, the diaper 101 may also contain a substantially hydrophilic tissue wrapsheet (not illustrated) that helps maintain the integrity of the fibrous structure of the absorbent core 103. The tissue wrapsheet is typically placed about the absorbent core 103 over at least the two major facing surfaces thereof, and composed of an absorbent cellulosic material, such as creped wadding or a high wet-strength tissue. The tissue wrapsheet may be configured to provide a wicking layer that helps to rapidly distribute liquid over the mass of absorbent fibers of the absorbent core 103. The wrapsheet material on one side of the absorbent fibrous mass may be bonded to the wrapsheet located on the opposite side of the fibrous mass to effectively entrap the absorbent core 103. Furthermore, the diaper 101 may also include a ventilation layer (not shown) that is positioned between the absorbent core 103 and the outer cover 117. When utilized, the ventilation layer may help insulate the outer cover 117 from the absorbent core 103, thereby reducing dampness in the outer cover 117. Examples of such ventilation layers may include a nonwoven web laminated to a breathable film, such as described in U.S. Pat. No. 6,663,611 to Blaney, et al., which is incorporated herein in its entirety by reference thereto for all purposes.

In some embodiments, the diaper 101 may also include a pair of side panels (or ears) (not shown) that extend from the side edges 132 of the diaper 101 into one of the waist regions. The side panels may be integrally formed with a selected diaper component. For example, the side panels may be integrally formed with the outer cover 117 or from the material employed to provide the top surface. In alternative configurations, the side panels may be provided by members connected and assembled to the outer cover 117, the top surface, between the outer cover 117 and top surface, or in various other configurations. If desired, the side panels may be elasticized or otherwise rendered elastomeric by use of the elastic nonwoven composite of the present invention. Examples of absorbent articles that include elasticized side panels and selectively configured fastener tabs are described in PCT Patent Application WO 95/16425 to Roessler; U.S. Pat. No. 5,399,219 to Roessler et al.; U.S. Pat. No. 5,540,796 to Fries; and U.S. Pat. No. 5,595,618 to Fries, each of which is incorporated herein in its entirety by reference thereto for all purposes.

As representatively illustrated in FIG. 1, the diaper 101 may also include a pair of containment flaps 112 that are configured to provide a barrier and to contain the lateral flow of body exudates. The containment flaps 112 may be located along the laterally opposed side edges 132 of the bodyside liner 105 adjacent the side edges of the absorbent core 103. The containment flaps 112 may extend longitudinally along the entire length of the absorbent core 103, or may only extend partially along the length of the absorbent core 103. When the containment flaps 112 are shorter in length than the absorbent core 103, they may be selectively positioned anywhere along the side edges 132 of diaper 101 in a crotch region 110. In one embodiment, the containment flaps 112 extend along the entire length of the absorbent core 103 to better contain the body exudates. Such containment flaps 112 are generally well known to those skilled in the art. For example, suitable constructions and arrangements for the containment flaps 112 are described in U.S. Pat. No. 4,704,116 to Enloe, which is incorporated herein in its entirety by reference thereto for all purposes.

To provide improved fit and to help reduce leakage of body exudates, the diaper 101 may be elasticized with suitable elastic members, as further explained below. For example, as representatively illustrated in FIG. 1, the diaper 101 may include leg elastics 106 constructed to operably tension the side margins of the diaper 101 to provide elasticized leg bands which can closely fit around the legs of the wearer to reduce leakage and provide improved comfort and appearance. Waist elastics 108 may also be employed to elasticize the end margins of the diaper 101 to provide elasticized waistbands. The waist elastics 108 are configured to provide a resilient, comfortably close fit around the waist of the wearer.

The diaper 101 may also include one or more fasteners 130. For example, two flexible fasteners 130 are illustrated in FIG. 1 on opposite side edges of waist regions to create a waist opening and a pair of leg openings about the wearer. The shape of the fasteners 130 may generally vary, but may include, for instance, generally rectangular shapes, square shapes, circular shapes, triangular shapes, oval shapes, linear shapes, and so forth. The fasteners may include, for instance, a hook-and-loop material, buttons, pins, snaps, adhesive tape fasteners, cohesives, fabric-and-loop fasteners, etc. In one particular embodiment, each fastener 130 includes a separate piece of hook material affixed to the inside surface of a flexible backing.

The various regions and/or components of the diaper 101 may be assembled together using any known attachment mechanism, such as adhesive, ultrasonic, thermal bonds, etc. Suitable adhesives may include, for instance, hot melt adhesives, pressure-sensitive adhesives, and so forth. When utilized, the adhesive may be applied as a uniform layer, a patterned layer, a sprayed pattern, or any of separate lines, swirls or dots. In the illustrated embodiment, for example, the outer cover 117 and bodyside liner 105 are assembled to each other and to the absorbent core 103 using an adhesive. Alternatively, the absorbent core 103 may be connected to the outer cover 117 using conventional fasteners, such as buttons, hook and loop type fasteners, adhesive tape fasteners, and so forth. Similarly, other diaper components, such as the leg elastic members 106, waist elastic members 108 and fasteners 130, may also be assembled into the diaper 101 using any attachment mechanism.

Generally speaking, the lateral flow assay device may be incorporated into the absorbent article in a variety of different orientations and configurations, so long as the device is capable of receiving the bodily fluid and providing a signal to a user or caregiver of the presence or absence of the analyte. For example, the detection zone and/or control zone are normally visible to the user or caregiver so that a simple, accurate, and rapid indication of the presence of the analyte may be provided. The visibility of such zone(s) may be accomplished in a variety of ways. For example, in some embodiments, the absorbent article may include a transparent or translucent portion (e.g., window, film, etc.) that allows the detection zone and/or control zone to be readily viewed without removal of the absorbent article from the wearer and/or without disassembly of the absorbent article. In other embodiments, the detection zone and/or control zone may extend through a hole or aperture in the absorbent article for observation. In still other embodiments, the detection zone and/or control zone may simply be positioned on a surface of the absorbent article for observation.

Referring now to FIGS. 1 and 6, in accordance with an exemplary embodiment of the present invention, the diaper 101 includes a lateral flow assay device 120 that may be positioned at least partially between the outer cover 117 and the absorbent core 103. The lateral flow assay device 120 may be positioned such that the detection zone 136 and control zone 138 are visible through a window 140 in the outer cover 117. The sample zone 142, positioned at one end of the assay device 120, is strategically positioned in the diaper 101 so that urine discharged by the wearer can travel to the sample zone 142 for collection of at least a portion of the discharged urine therein. The absorbent material 154 is also provided at the other end of the assay device 120 to hold part of the sample and to promote wicking or capillary flow in the device 120 as will be more fully described below.

FIG. 1 illustrates the assay device 120 as being placed directly into the layers that comprise the absorbent article 101. Alternatively, the assay device 120 may be partially or completely encased within a thin film (not shown) except for the sample zone 142, which remains exposed to the bodily fluid (e.g., urine) being tested. Such embodiments may be desirable so as to inhibit other components of the assay device 120, other than the sample zone 142, from receiving the bodily fluid directly from the wearer or from the layers of the absorbent article 101. For example, the assay device 120 may operate more effectively if the wicking zone 154 is shielded so that it draws the bodily fluid only from sample zone 142 and not from the absorbent article 101. Such thin film may be constructed, for example, from a variety of materials including polymers such as polyethylene, polypropylene, polycarbonate, and others.

As stated, the assay device 120 is positioned so as to receive the discharged bodily fluid. As shown, the assay device 120 includes a sample zone 142 for collection of the fluid. Alternatively, the sample zone for assay device 120 may be constructed from one or more components that form parts of the absorbent article 101. By way of example, the sample zone could be constructed as part of the surge layer 107, absorbent core 103, or other components that might be used in the construction of absorbent article 101 and that are capable of receiving and providing fluid to assay device 120.

The assay device 120 may be configured with the diaper 101 in a variety of different placements and orientations. FIG. 1 depicts the assay device 120 at a position between the absorbent core 103 and the outer cover 117. In this manner, the zones 136 and 138 are visible though the window 140 when the diaper 101 is in place on the wearer. The window 140 is made of a transparent material formed as part of the outer cover 117 so as to prevent undesirable leaks of the collected fluids. In such cases, the results of testing with the device 120 may be readily observed without removal of the diaper 101 from the wearer. Alternatively, the device 120 could be placed between, for example, the absorbent core 103 and the bodyside liner 105 with the window 140 being defined by the bodyside liner 105. In such cases, the results of testing with the assay device 120 may be checked when, for example, the diaper 101 is being changed or replaced on the wearer. Furthermore, the device 120 may be placed at other locations and in different orientations as well.

Figure 2:
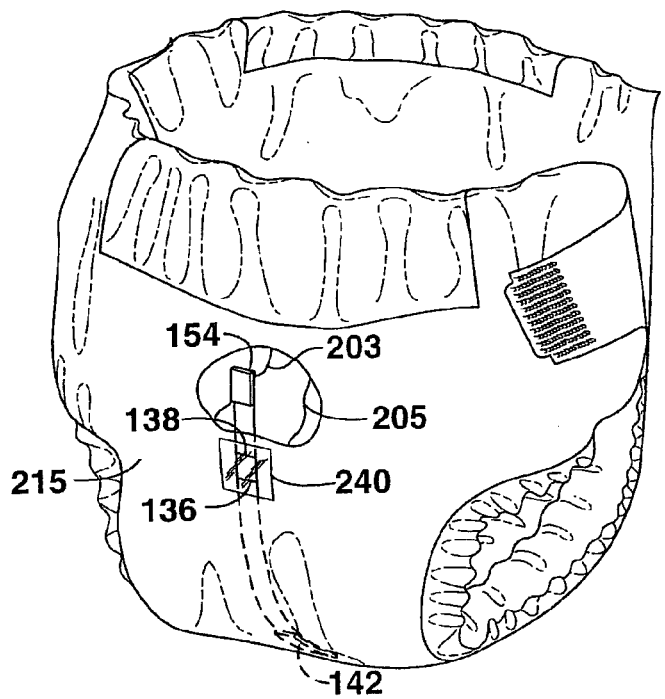
FIG. 2 is perspective view and partial cut-away view of another exemplary embodiment according to the present invention.

In fact, as will be understood using the present disclosure, numerous exemplary embodiments exist for integrating the assay device 120 into an absorbent article as will be further described. For example, FIG. 2 depicts another exemplary embodiment of the present invention in which the assay device 120 has been integrated into a diaper 215. Here, a window 240 allows observations of the detection zone 136 and the control zone 138 as previously described. Compared to FIG. 1, the assay device 120 has been placed on an opposite side of the diaper 101.

Figure 3:
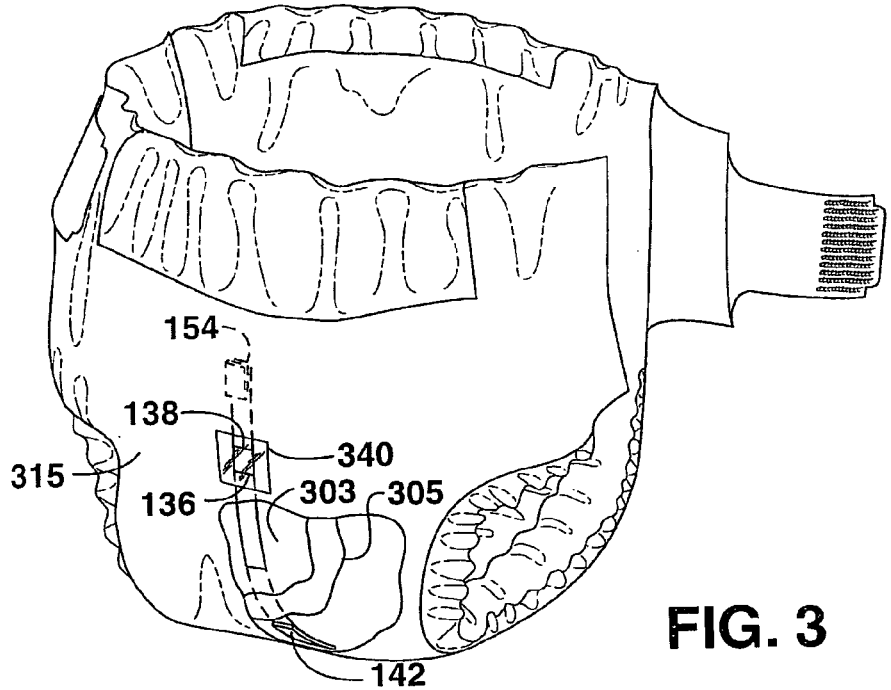
FIG. 3 is perspective view and partial cut-away view of another exemplary embodiment according to the present invention.

FIG. 3 illustrates another exemplary embodiment where the assay device 120 has been integrated into a diaper 315. Again, a window 340 allows observations of the detection zone 136 and the control zone 138 as previously described. In a manner similar to FIG. 1 and FIG. 2, the wicking zone 154 is placed next to the outer cover 117. However, in contrast to FIG. 1 and FIG. 2, the sample zone 142 is placed next to the wearer's skin. More specifically, the diaper 315 is constructed with the assay device 120 extending through absorbent core 303 and body side liner 305 to a position where sample zone 142 will be adjacent the wearer's skin.

Figure 4:
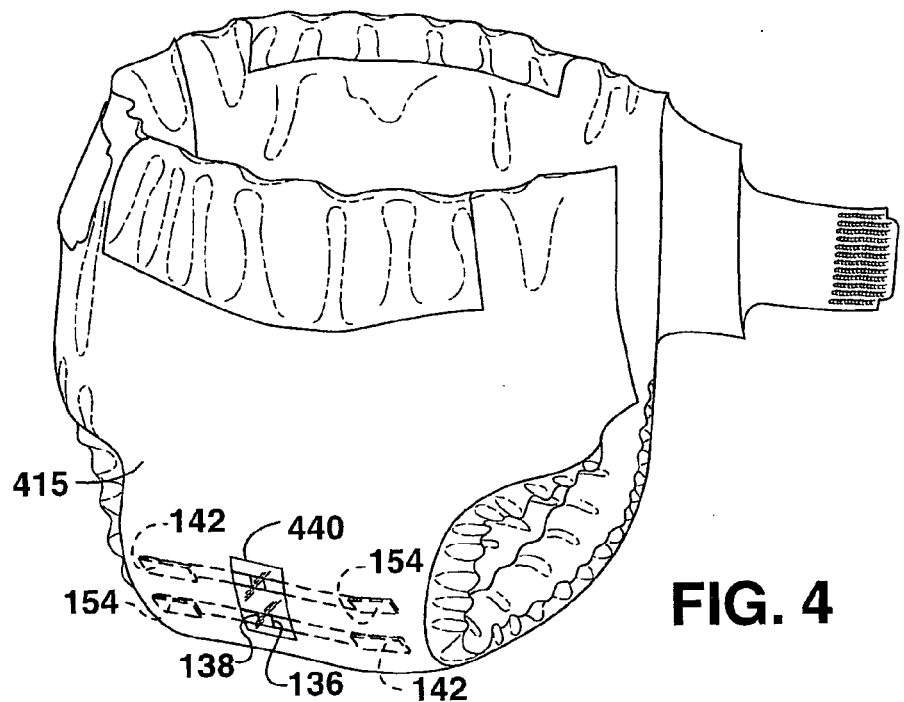
FIG. 4 is perspective view of another exemplary embodiment according to the present invention.

FIG. 4 illustrates a diaper 415 having two assay devices 120 integrated therein. As shown, window 440 allows the detection zone 136 and control zone 138 of two different assay devices 120 to be observed from outside the diaper 415. Such configuration might be desirable, for example, were each assay device 120 is constructed for detecting the presence of different analytes. In addition, the assays devices in FIG. 4 are oriented at an obtuse angle relative to the embodiments of FIGS. 1 through 3. Thus, FIG. 4 also illustrates that multiple configurations and orientations for devices 120 may be utilized under the teachings disclosed herein.

Figure 5:
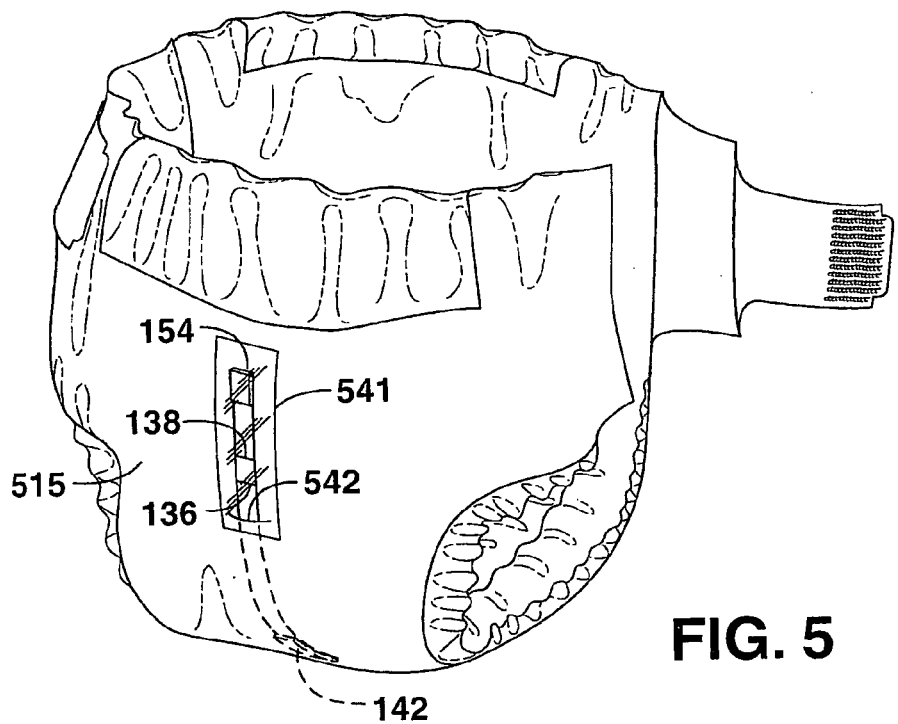
FIG. 5 is perspective view of another exemplary embodiment according to the present invention.

FIG. 5 shows the assay device 120 incorporated into a diaper 515. Rather than being visible through a window, the detection zone 136 and control zone 138 are actually on the outside of the diaper 515. The sample zone 142 resides inside the diaper 515 as part of the assay device 120 and extends through an aperture 542 in a cover 517. A transparent film 541 is affixed to the cover 517 to protect the assay device 120 and prevent fluid leaks from diaper 515.

For each of the embodiments described above, the assay device 120 may be fixed into position in the absorbent article using a variety of techniques or mechanisms. For example, the assay device 120 may be attached using any known attachment mechanism, such as adhesive, ultrasonic, thermal bonds, etc. Suitable adhesives may include, for instance, hot melt adhesives, pressure-sensitive adhesives, and so forth. When utilized, the adhesive may be applied as a uniform layer, a patterned layer, a sprayed pattern, or any of separate lines, swirls or dots. Alternatively, the assay device 120 may be connected using conventional fasteners, such as buttons, hook and loop type fasteners, adhesive tape fasteners, and so forth. By way of further example, pockets or apertures may be built into one or more layers of the absorbent article to fix the position of the assay device 120. In short, a variety of configurations may be used to secure assay device 120 into a position that helps ensure contact with the bodily fluid to be tested.

Again, the embodiments of FIGS. 1 through 6 are provided by way of example only as the present invention is not limited to a diaper and may be used with other absorbents articles as well. In addition, numerous configurations and variations of an assay device may be used. Such assay devices may be incorporated in a variety of orientations and configurations into such absorbent articles.

Regardless of the particular manner in which it is integrated, a fluid such as urine may be directly discharged to a portion of chromatographic medium 123, a liquid permeable cover or other material surrounding assay device 120, or may be discharged onto a component of the absorbent article into which the assay device 120 has been integrated. Once the fluid reaches chromatographic medium 123, the fluid may then travel in the direction illustrated by arrow "L" in FIG. 6. Alternatively, the test sample may first be applied to, or supplied to, a sample application zone 142 that is in fluid communication with the chromatographic medium 123. The sample application zone 142 may be formed on the medium 123. Alternatively, as shown in FIG. 1, the sample application zone 142 may be formed by a separate material, such as a pad.

After a sufficient reaction time, the intensity of the color at the detection zone 136 may be measured to quantitatively or semi-quantitatively determine the level of analyte present in the test sample. Nevertheless, while quantitative testing may be performed, qualitative testing is typically employed to provide early testing and monitoring of a health condition. Thus, when one or more analytes of interest are visually detected, the user or caregiver is given an indication that further quantitative testing may be undertaken. For example, a diaper having an integrated assay device may be periodically used with infants or non-ambulatory patients as part of a monitoring program that tests for UTI. Upon indication of a positive test result, further quantitative testing can then be undertaken to determine the scope and stage of the problem detected so a to provide additional treatment information.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. An absorbent article for receiving urine suspected of containing a leukocyte esterase that is indicative of the presence of urinary tract infection, comprising:
   a substantially liquid impermeable layer;
   a liquid permeable layer;
   an absorbent core positioned between the substantially liquid impermeable layer and the liquid permeable layer; and
   a lateral flow assay device positioned between the substantially liquid impermeable layer and the absorbent core such that the device is in fluid communication with urine when provided by a wearer of the article, the lateral flow assay device comprising a chromatographic medium that defines a detection zone, wherein a capture reagent is substantially non-diffusively immobilized within the detection zone that is configured for exhibiting a signal indicative of the presence or absence of the leukocyte esterase in the urine, and wherein the device further comprises a sample application zone that is in fluid communication with the absorbent core and is configured to directly receive the urine therefrom, wherein the detection zone is separate and distinct from the sample application zone and located laterally downstream therefrom.

2. The absorbent article of claim 1, wherein the lateral flow assay device includes a control zone for indicating that a sufficient volume of the urine has been received by the lateral flow assay device, wherein the control zone is separate and distinct from the sample application zone and located downstream therefrom.

3. The absorbent article of claim 2, further comprising a control reagent that is capable of being detected within the control zone.

4. The absorbent article of claim 2, wherein the absorbent article defines a window through which the detection zone, the control zone, or both are observable.

5. The absorbent article of claim 1, wherein the sample application zone is comprised of at least part of the absorbent core.

6. The absorbent article of claim 1, wherein the lateral flow assay device is adhered to the absorbent core.

7. The absorbent article of claim 1, wherein the lateral flow assay device extends at least partially through an aperture so that the detection zone is located outside of the absorbent article.

8. The absorbent article of claim 1, wherein the capture reagent is a specific binding member.

9. The absorbent article of claim 1, wherein the capture reagent is a diazonium ion or a derivative thereof.

10. The absorbent article of claim 1, wherein the lateral flow assay device further comprises a diffusively immobilized reagent.

11. The absorbent article of claim 10, wherein the diffusively immobilized reagent includes a specific binding member.

12. The absorbent article of claim 10, wherein the diffusively immobilized reagent includes an aromatic ester substrate.

13. The absorbent article of claim 1, wherein the lateral flow assay device includes an absorbent material that receives the urine after flowing through the chromatographic medium.

14. A diaper for receiving urine suspected of containing a leukocyte esterase that is indicative of the presence of urinary tract infection, the diaper comprising:
   an outer cover;
   a bodyside liner joined to the outer cover;
   an absorbent core positioned between the outer cover and the bodyside liner; and
   a lateral flow assay device positioned between the substantially liquid impermeable layer and the absorbent core such that the device is in fluid communication with the urine when provided by a wearer of the article, the lateral flow assay device comprising a porous membrane that defines a detection zone, wherein a capture reagent is substantially non-diffusively immobilized within the detection zone that is configured for exhibiting a signal indicative of the presence or absence of the leukocyte esterase in the urine, and wherein the device further comprises a sample application zone that is in fluid communication with the absorbent core and is configured to directly receive urine therefrom, wherein the detection zone is separate and distinct from the sample application zone and located laterally downstream therefrom.

15. The diaper of claim 14, wherein the lateral flow assay device includes a control zone for indicating that a sufficient volume of the urine has been received by the lateral flow assay device, wherein the control zone is separate and distinct from the sample application zone and located downstream therefrom.

16. The diaper of claim 15, further comprising a control reagent that is capable of being detected within the control zone.

17. The diaper of claim 16, wherein the diaper defines a window through which the detection zone, the control zone, or both are observable.

18. The diaper of claim 14, wherein the sample application zone is comprised of at least part of the absorbent core.

19. The diaper of claim 14, wherein the lateral flow assay device is adhered to the absorbent core.

20. The diaper of claim 14, wherein the lateral flow assay device extends at least partially through an aperture so that the detection zone is located outside of the diaper.

21. The diaper of claim 14, wherein the lateral flow assay device further comprises a diffusively immobilized reagent.

22. The diaper of claim 14, wherein the lateral flow assay device further comprises an absorbent material that receives the urine after flowing through the porous membrane.

* * * * *

UNITED STATES PATENT AND TRADEMARK OFFICE
CERTIFICATE OF CORRECTION

PATENT NO.        : 8,044,257 B2
APPLICATION NO.   : 11/589671
DATED             : October 25, 2011
INVENTOR(S)       : Xuedong Song Page 1 of 1

It is certified that error appears in the above-identified patent and that said Letters Patent is hereby corrected as shown below:

Title Page 2, U.S. Patent Documents, Column 1, below "5,663,044 A 9/1997 Noffsinger et al." insert -- 5,670,381 09/1997 Jou et al. --

Signed and Sealed this
Fifteenth Day of January, 2013

David J. Kappos
*Director of the United States Patent and Trademark Office*